US010429345B2

(12) United States Patent
Ichiki et al.

(10) Patent No.: US 10,429,345 B2
(45) Date of Patent: Oct. 1, 2019

(54) ELECTROPHORESIS DEVICE, METHOD FOR MANUFACTURING ELECTROPHORESIS DEVICE, AND DEVICE FOR SEPARATING EXTRACELLULAR VESICLES

(71) Applicant: The University of Tokyo, Tokyo (JP)

(72) Inventors: Takanori Ichiki, Tokyo (JP); Takanori Akagi, Tokyo (JP); Ryosuke Kubota, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 328 days.

(21) Appl. No.: 15/503,215

(22) PCT Filed: Aug. 28, 2015

(86) PCT No.: PCT/JP2015/074497

§ 371 (c)(1),
(2) Date: Feb. 10, 2017

(87) PCT Pub. No.: WO2016/031980

PCT Pub. Date: Mar. 3, 2016

(65) Prior Publication Data

US 2017/0234832 A1 Aug. 17, 2017

Related U.S. Application Data

(60) Provisional application No. 62/043,149, filed on Aug. 28, 2014.

(51) Int. Cl.

*G01N 27/453* (2006.01)
*G01N 27/447* (2006.01)

(Continued)

(52) U.S. Cl.

CPC .... *G01N 27/44721* (2013.01); *B01L 3/50273* (2013.01); *G01N 1/10* (2013.01);

(Continued)

(58) Field of Classification Search

CPC .................. G01N 27/44769; G01N 27/44791

See application file for complete search history.

(56) References Cited

U.S. PATENT DOCUMENTS

2009/0218222 A1* 9/2009 Manz .............. G01N 27/44782 204/545

FOREIGN PATENT DOCUMENTS

EP 2 889 623 A1 7/2015
JP 2003-66005 A 3/2003

(Continued)

OTHER PUBLICATIONS

Jezierski et al., "Multistep liquid=phase lithography for fast prototyping of microfluidic free-flow-electrophoresis chip," Anal. Bioanal. Chem. (2011) 401:2651-2656 (Year: 2011).*

(Continued)

*Primary Examiner* — Alexander S Noguerola
(74) *Attorney, Agent, or Firm* — Westerman, Hattori, Daniels & Adrian, LLP

(57) ABSTRACT

Electrophoresis device including: a first flow passage extending in a first direction and through which a sample and a buffer solution flow; a sample collecting part provided at an end portion of the first flow passage and configured to collect the sample; electrodes disposed at both sides of the first flow passage in a second direction perpendicular to the first direction and configured to apply a voltage to the first flow passage in the second direction; second flow passages communicating with both sides of the first flow passage in the second direction, configured to accommodate the electrodes, and through which a second buffer solution flows;

(Continued)

and partition walls fixed to communicating portions between the first and second flow passages with a predetermined bonding strength and configured to block movement of substances between the first and second flow passages. The partition walls are formed of a gel material having ion permeability.

11 Claims, 12 Drawing Sheets

(51) Int. Cl.
*G01N 1/10* (2006.01)
*G01N 1/40* (2006.01)
*G01N 33/53* (2006.01)
*G01N 33/566* (2006.01)
*G01N 15/14* (2006.01)
*B01L 3/00* (2006.01)
*G01N 15/00* (2006.01)
*G01N 15/10* (2006.01)

(52) U.S. Cl.
CPC ............. *G01N 1/40* (2013.01); *G01N 1/4077* (2013.01); *G01N 15/1429* (2013.01); *G01N 15/1459* (2013.01); *G01N 15/1463* (2013.01); *G01N 27/447* (2013.01); *G01N 27/44713* (2013.01); *G01N 27/44743* (2013.01); *G01N 27/44791* (2013.01); *G01N 33/5308* (2013.01); *G01N 33/566* (2013.01); *G01N 27/44769* (2013.01); *G01N 2001/4038* (2013.01); *G01N 2015/0003* (2013.01); *G01N 2015/1006* (2013.01)

(56) References Cited

FOREIGN PATENT DOCUMENTS

| | | |
|---|---|---|
| JP | 2004-294334 A | 10/2004 |
| WO | 2014/030590 A1 | 2/2014 |

OTHER PUBLICATIONS

JPO computer-generated English language translation of JP 2003-066005(a). Downloaded Feb. 27, 2019. (Year: 2019).*

Kohlheyer et al., “Miniaturizing free-flow electrophoresis—a critical review”, Electrophoresis, 2008, vol. 29, pp. 977-993, (17 pages).

Turgeon et al., “Micro free-flow electrophoresis: theory and applications”, Anal Bioanal Chem, 2009, vol. 394, pp. 187-198, (12 pages).

Hannig, “Die trägerfreie kontinuierliche Elektrophmrese und ihre Anwendung”, Fresenius’ Zeitschrift fur analytische Chemie, 1961, vol. 181, pp. 244-254, w/English partial translation (12 pages).

Raymond et al., “Continuous Sample Pretreatment Using a Free-Flow Electrophoresis Device Integrated onto a Silicon Chip”, Anal Chem, 1994, vol. 66, pp. 2858-2865, (8 pages).

Albrecht et al., “Micro free-flow IEF enhanced by active cooling and functionalized gels”, Electrophoresis, 2006, vol. 27, pp. 4960-4969, (12 pages).

Jesus et al., “Microchip free-flow electrophoresis on glass substrate using laser-printing toner as structural material”, Electrophoresis, 2006, vol. 27, pp. 4935-4942, (8 pages).

Kohlheyer et al., “Free-flow zone electrophoresis and isoelectric focusing using a microfabricated glass device with on permeable membranes”, Lab on a Chip, 2006, vol. 6, pp. 374-380, (7 pages).

Köhler et al., “PDMS free-flow electrophoresis chips with integrated partitioning bars for bubble segregation”, Lab on a Chip, 2010, vol. 11, pp. 309-314, cited in ISR (6 pages).

Song et al., “Free-Flow Zone Electrophoresis of Peptides and Proteins in PDMS Microchip for Narrow pl Range Sample Prefractionation Coupled with Mass Spectrometry”, Anal Chem., Mar. 15, 2010, vol. 82, No. 6, pp. 2317-2325, cited in ISR (16 pages).

Puchberger-Enengl et al., “Microfluidic concentration of bacteria by on-chip electrophoresis”, Biomicrofluidics, 2011, vol. 5, No. 044111, pp. 044111-1-044111-10, cited in ISR (10 pages).

International Search Report dated Nov. 10, 2015, issued in counterpart International Application No. PCT/JP2015/074497, w/English translation (4 pages).

* cited by examiner

ELECTROPHORESIS DEVICE, METHOD FOR MANUFACTURING ELECTROPHORESIS DEVICE, AND DEVICE FOR SEPARATING EXTRACELLULAR VESICLES

Priority is claimed on U.S. Provisional Application No. 62/043,149, filed Aug. 28, 2014, the content of which is incorporated herein by reference.

TECHNICAL FIELD

The present invention relates to an electrophoresis device, a method for manufacturing an electrophoresis device, and a device for separating extracellular vesicles.

BACKGROUND ART

Molecules such as nucleic acids, proteins, and lipids, molecular aggregates such as intracellular organelles and extracellular vesicles, and cells, which are derived from a living body, are analysis targets when mechanisms of a physiological phenomenon and a pathological phenomenon are explained and an effect at a time at which drug treatment is performed is quantitatively evaluated.

Generally, a plurality of different components such as molecules, molecular aggregates, particles, and cells are mixed in a sample extracted from a living body. Thus, it is necessary to separate/purify only a component serving as an analysis target. Physical properties such as a size, a specific gravity, a water/oil distribution coefficient, an isoelectric point, and a surface potential or molecule affinity (affinity) can be used as indexes when a component in a sample is separate/purified.

As a method for performing separation/purification using a surface potential, a free flow electrophoresis method is known (refer to Non-Patent Literature 1).

A free flow electrophoresis method is technology in which a voltage is applied to electrodes provided at both sides of a separation tank while a sample flows in the separation tank from an upstream side to a downstream side in a laminar flow shape together with a buffer solution such that an electric field is applied to a splitting tank in a direction perpendicular to a flow of the buffer solution, the sample is subject to free zone electrophoresis, and a component in the sample is separated using a difference between electrophoretic mobility of components in the sample.

According to a free flow electrophoresis method, components mixed in a sample can be separated/purified using a difference between surface potentials (electrophoretic mobility) of the components. Furthermore, a specific component can also be arbitrarily separated by bonding molecule tags having a specific affinity, such as antibodies, to components in the sample and using a change of the surface potential occurring as a result of the bonding of the antibodies to the components.

A free flow electrophoresis device in the related art is large and needs a large amount of a sample to separate components mixed in the sample, for example, extracellular vesicles such as exosomes (refer to Non-Patent Literature 2). Furthermore, the free flow electrophoresis device in the related art is expensive. In order to solve such problems, development research of a small-sized free flow electrophoresis device (a micro-free flow electrophoresis chip) to which micro-fluidic device technology is applied has been recently conducted. In addition, it is disclosed that a prototype small-sized free flow electrophoresis device is effective in separating a small amount of a sample (refer to Non-Patent Literature 3).

In a free flow electrophoresis device using micro-fluidic device technology, there are problems in that an influence of bubbles occurring on electrodes due to electrolysis is large and a stable operation for a long period of time may be difficult in some cases. In order to solve such problems, a method for separating a separation tank and an electrode tank using a gel with ion permeability and removing bubbles by refluxing a sample in an electrode tank without disturbing a laminar flow in the separation tank is suggested (refer to Non-Patent Literature 4).

CITATION LIST

Patent Literature

[Non-Patent Literature 1]
D Kohlheyer, et al., Electrophoresis, 29, 977 to 993, 2008; RT Turgeon, et al., Anal Bioanal Chem, 394, 187 to 198, 2009
[Non-Patent Literature 2]
K Hannig. Anal Chem, 181, 244 to 254, 1961
[Non-Patent Literature 3]
DE Raymond, et al., Anal Chem, 66, 2858 to 2865, 1994
[Non-Patent Literature 4]
J W Albrecht, et al., Electrophoresis 27, 4960 to 4969, 2006; DP de Jesus, et al., Electrophoresis, 27, 4935 to 4942, 2006; D Kohlheyer, et al., Lab Chip 6, 374 to 380, 2006

SUMMARY OF INVENTION

Technical Problem

In the case of agarose gels or acrylamide gels used in the above-described literatures, there are problems in that the agarose gels or the acrylamide gels are not chemically bonded to silicon or glass serving as a base material subject to a micro-free flow electrophoresis method, peeling at an interface between a hydrogel and the base material easily occurs, and thus a stable operation for a long period of time is difficult.

The present invention was made in view of the above-described circumstances, and the present invention is for the purpose of providing an electrophoresis device which can stably operate, a method for manufacturing an electrophoresis device, and a device for separating extracellular vesicles.

Solution to Problem

According to a first aspect of the present invention, provided is an electrophoresis device including: a first flow passage extending in a first direction and through which a sample and a buffer solution flow; a sample collecting part provided at an end portion of the first flow passage and configured to collect the sample; electrodes disposed at both sides of the first flow passage in a second direction perpendicular to the first direction and configured to apply a voltage to the first flow passage in the second direction; second flow passages communicating with both sides of the first flow passage in the second direction, configured to accommodate the electrodes, and through which a second buffer solution flows; and partition walls fixed to communicating portions between the first and second flow passages with a predetermined bonding strength and configured to block movement of substances between the first and second flow passages, wherein the partition walls are formed of a gel material having ion permeability.

According to a second aspect of the present invention, provided is a device for separating extracellular vesicles including: the electrophoresis device according to the first aspect of the present invention; a sample supply system configured to supply a sample including extracellular vesicles to the first flow passage; a buffer solution supply system configured to supply the buffer solution to the first flow passage; a sample collecting system configured to collect the sample via the sample collecting part; a second buffer solution supply system configured to supply the second buffer solution to one ends of the second flow passages; a second flow passage collecting system configured to collect substances in the second flow passages from the other ends of the second flow passages; and an adjusting part configured to adjust the voltage applied through the electrodes.

According to a third aspect of the present invention, provided is a method for manufacturing an electrophoresis device including: a step of preparing a base material including a first flow passage extending in a first direction and through which a sample and a buffer solution flow and second flow passages communicating with both sides of the first flow passage in a second direction and through which a second buffer solution flows; and a step of fixing a gel material having ion permeability to communicating portions between the first flow passage and the second flow passages as partition walls configured to block movement of substances between the first flow passage and the second flow passages with a predetermined bonding strength.

Advantageous Effects of Invention

According to the present invention, an electrophoresis device which can stably operate for a long period of time, a method for manufacturing an electrophoresis device, and a device for separating extracellular vesicles can be provided.

DESCRIPTION OF EMBODIMENTS

Figure 1:
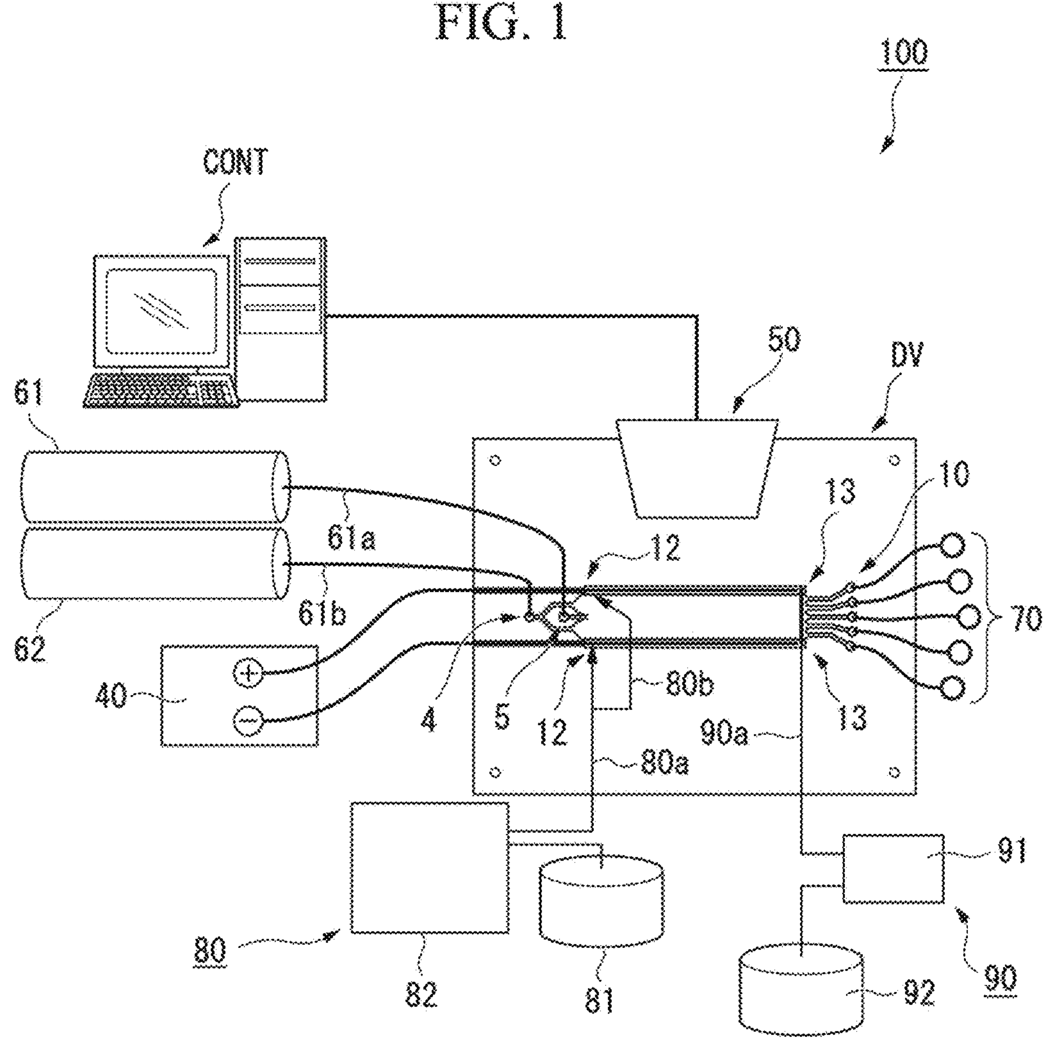
FIG. 1 is a schematic constitution diagram of a device for separating extracellular vesicles related to an embodiment.

Hereinafter, embodiments of an electrophoresis device, a method for manufacturing an electrophoresis device, and a device for separating extracellular vesicles, which are related to the present invention will be described with reference to FIGS. 1 to 21.

Note that the following embodiment indicates an aspect of the present invention and does not limit the present invention. In addition, modification is arbitrarily possible within a range of the technical idea of the present invention. Also, in the following drawings, an actual structure and a scale, a number, and the like of structures may be differentiated to facilitate the understanding of the constitutions.

In an embodiment, the present invention provides an electrophoresis device used when a sample (a specimen) is separated. Examples of the specimen include cells, extracellular vesicles, microparticles, latex particles (including latex particles modified with antibodies and further modified with cells), polymeric micelles, and the like. In this embodiment, a case in which a device for separating extracellular vesicles is used as the electrophoresis device to separate extracellular vesicles will be described. In this specification, the extracellular vesicles refer to lipid vesicles including exosomes, apoptotic bodies, microvesicles, or the like. Hereinafter, the device for separating extracellular vesicles and the electrophoresis device, which are related to this embodiment, will be described using a case in which exosomes are separated as an example.

[Exosomes]

Exosomes are lipid vesicles having a diameter of about 30 to 100 nm and are secreted into a body fluid such as blood, urine, and saliva from various cells such as tumor cells, dendritic cells, T cells, and B cells as fused bodies of endosomes and cell membranes.

Abnormal cells such as cancer cells present in a living body express a protein specific to cell membranes thereof. The exosomes are secretions of cells and express proteins derived from the cells serving as secretory source on surfaces of the exosomes.

Abnormality of the cells serving as the secretory sources can be detected by analyzing the proteins expressed on the surfaces of the exosomes. Here, the surfaces of the exosomes are membrane surfaces of lipid vesicles secreted from the cells and refer to portions at which the secreted exosomes come into contact with an environment inside the living body.

Abnormality in the living body can be detected without a biopsy check by analyzing the exosomes because the exosomes are detected in blood circulating in the living body.

[Analysis of Exosomes]

Analysis of exosomes using the electrophoresis device can be performed as will be described as an example. First, exosomes to be detected are separated and purified. Subsequently, the exosomes are brought into contact with a specific binding substance. Here, the specific binding substance refers to a substance which can specifically bind to molecules present on surfaces of the exosomes. Subsequently, the analysis thereof is performed by measuring zeta potentials of the exosomes using the electrophoresis device. This analysis can be applied not only to the exosomes but also widely to a general analysis of extracellular vesicles.

(Specific Binding Substance)

Examples of the specific binding substance include antibodies, modified antibodies, aptamers, ligand molecules, and the like. Examples of the antibodies include IgG, IgA, IgD, IgE, IgM, and the like. Examples of IgG include IgG1, IgG2, IgG3, IgG4, and the like. Examples of IgA include IgA1, IgA2, and the like. Examples of IgM include IgM1, IgM2, and the like. Examples of the modified antibodies include Fab, F(ab')2, scFv, and the like. Examples of the aptamers include peptide aptamers, nucleic acid aptamers, and the like. Examples of the ligand molecules include ligands and the like of receptor proteins when molecules to be detected that are present on the surfaces of the exosomes are the receptor proteins. For example, when the molecules present on the surfaces of the exosomes are interleukins, examples of the ligand molecules include G proteins and the like.

Also, the specific binding substance may be labeled with a labeling substance. Examples of the labeling substance include charged molecules, such as biotin, avidin, streptavidin, neutravidin, glutathione-S-transferase, glutathione, a fluorescent dye, polyethylene glycol, mellitic acid, and the like.

(Separation/Purification of Exosomes)

Steps of this analysis will be described. First, exosomes are purified from a sample containing the exosomes. Examples of the sample include blood, urine, breast milk, a bronchoalveolar lavage fluid, an amniotic fluid, a malignant exudate, saliva, a cell culture solution, and the like in accordance with a purpose of the analysis. Among them, exosomes are easily purified from blood and urine.

A method for purifying exosomes is performed using an electrophoresis device DV related to this embodiment as will be described later.

(Reaction Between Exosomes and Specific Binding Substance)

Subsequently, the exosomes are brought into contact with a specific binding substance (antibodies, aptamers, or the like). When molecules to be detected are present on surfaces of the exosomes, a specific binding substance-exosome composite is formed. Abnormality associated with diseases such as, for example, cancer, obesity, diabetes, and neurodegenerative diseases can be detected by appropriately selecting the specific binding substance. A detailed description thereof will be described below.

(Measurement of Zeta Potentials)

As an example, a case in which antibodies are used as a specific binding substance will be described. After exosomes and the antibodies are reacted with each other, zeta potentials of the exosomes reacting with the antibodies are measured. The zeta potentials are surface charges of microparticles in a solution. For example, while exosomes are negatively charged, antibodies are positively charged. For this reason, zeta potentials of an antibody-exosome composite are shifted positively compared with zeta potentials of independent exosomes. Therefore, an expression of antigens on membrane surfaces of the exosomes can be detected by measuring the zeta potentials of the exosomes reacting with the antibodies. This is true not only for the antibodies but also for a positively charged specific binding substance.

For example, electrophoresis is performed on exosomes in a micro-flow passage of the electrophoresis device, an electrophoresis speed S of the exosomes is optically measured, and a zeta potential of the exosomes can be calculated using Smoluchowski's equation represented by the following Expression (1) on the basis of the measured electrophoresis speed S of the exosomes.

$$U=(\varepsilon/\eta)\zeta \quad (1)$$

In Expression (1), U is electrophoresis mobility of exosomes to be measured, and $\varepsilon$ and $\eta$ are respectively a dielectric constant and a viscosity coefficient of a sample solution. Furthermore, the electrophoresis mobility U can be calculated by dividing the electrophoresis speed S by an electric field intensity in a micro-flow passage.

The electrophoresis speed S of the exosomes can be measured by, for example, subjecting the exosomes to electrophoresis in a micro-flow passage of an extracellular vesicle analysis chip or, for example, irradiating exosomes flowing in the micro-flow passage with a laser beam, and obtaining a particle image using Rayleigh scattered light. Examples of the laser beam include a beam with a wavelength of 488 nm and an intensity of 50 mW.

[Basic Structure of Device for Separating Extracellular Vesicles]

FIG. 1 is a schematic constitution diagram of a device 100 for separating extracellular vesicles.

The device 100 for separating extracellular vesicles includes the electrophoresis device DV, a voltage adjusting part (an adjusting part) 40, a microscope 50, a sample supply system 61, a buffer solution supply system 62, a sample collecting system 70, a second buffer solution supply system 80, a second flow passage collecting system 90, and a controller CONT.

[Electrophoresis Device DV]

Figure 2:
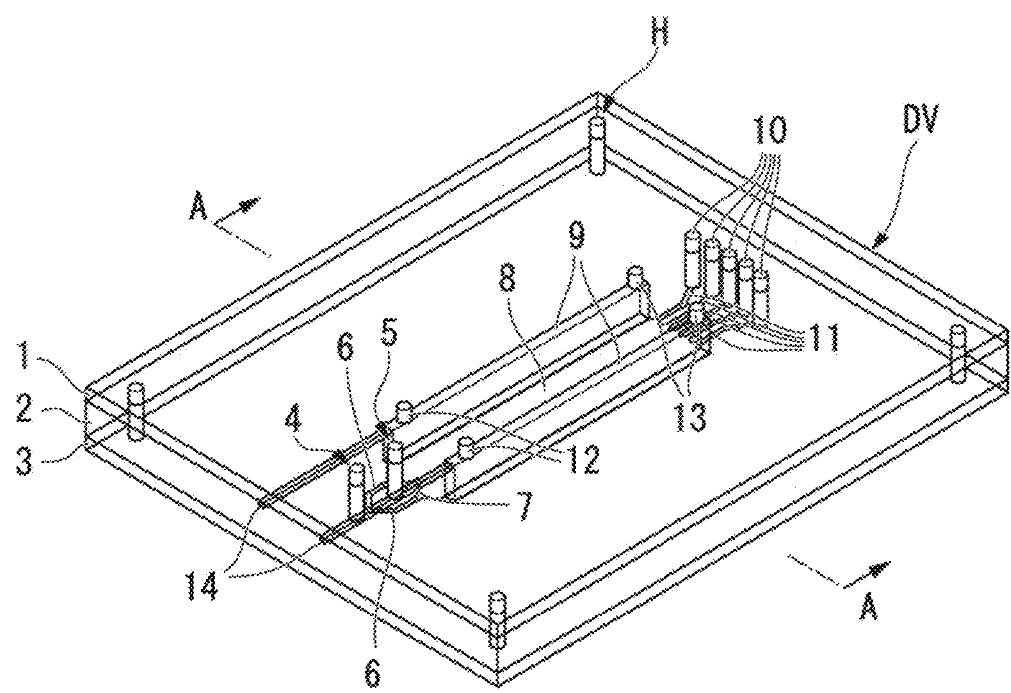
FIG. 2 is an exterior perspective view of an electrophoresis device DV related to an embodiment.
Figure 2:
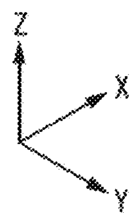
Figure 3:
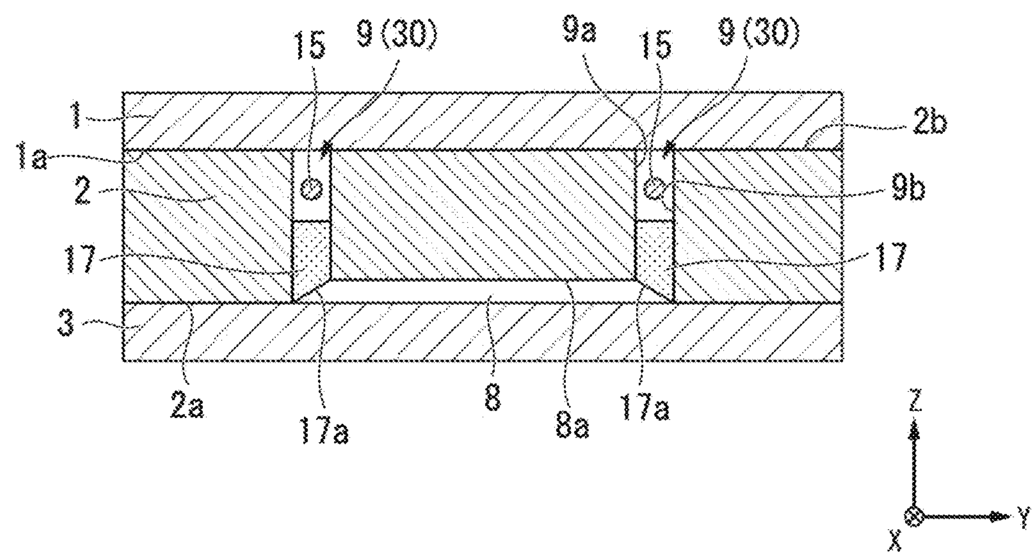
FIG. 3 is a cross-sectional view when viewed along line A-A in FIG. 2.

FIG. 2 is an exterior perspective view of the electrophoresis device DV. FIG. 3 is a cross-sectional view when viewed along line A-A in FIG. 2. Note that in FIG. 2, constituent elements of the electrophoresis device DV are indicated using a solid line to facilitate understanding.

As shown in FIG. 2, the electrophoresis device DV has a first substrate (a second base material) 1, a second substrate (a base material) 2, and a third substrate (a third base material) 3, which are sequentially stacked in a thickness direction and have rectangular shapes in a plan view. Through holes H for positioning are provided at corners of the first substrate 1, the second substrate 2, and the third substrate 3, and shaft members (not shown) are fitted into the through holes H such that the first substrate 1, the second substrate 2, and the third substrate 3 are mutually positioned.

The electrophoresis device DV includes a buffer solution introduction port 4, a sample introduction port 5, buffer solution introduction passages 6, a sample introduction passage 7, a separation tank (a first flow passage) 8, electrode tanks 9, sample collecting parts 10, sample collection passages 11, second buffer solution introduction ports 12, second buffer solution collection ports 13, and electrodes 15 (refer to FIGS. 3 and 8 to 10).

Note that, description in the following description is given under the assumption that a stacking direction of the first substrate 1, the second substrate 2, and the third substrate 3 is for example, a Z direction, a direction along which the separation tank 8 extends is an X direction, and a direction perpendicular to the Z direction and the X direction is a Y direction as well as a width direction of the separation tank 8. Also, the description is given in a state in which the Z direction is appropriately set to a vertical direction, a side at which the first substrate 1 is disposed with respect to the second substrate 2 is assumed to be an upper side, and a side at which the third substrate 3 is disposed with respect to the second substrate 2 is assumed to be a lower side. This is merely used to define the vertical direction for the sake of convenience of explanation and does not limit an installation posture when the electrophoresis device DV of the present invention is actually used.

The first substrate 1, the second substrate 2, and the third substrate 3 can be made of various industrial synthetic resins. Examples of the first substrate 1, the second substrate 2, and the third substrate 3 include polymethacryl styrene serving as a synthetic resinous material. Polymethacryl styrene is a resin extrusion plate of polymethacryl styrene (MS) obtained by subjecting methacrylate (MMA) and styrene to copolymerization. Main features of polymethacryl styrene include that it has excellent dimensional stability and is not easily deformed because it has transparency and weather resistance corresponding to those of a polymethacrylic board and has water absorptivity smaller than that of the polymethacrylic board, that it has a specific gravity which is even smaller than that of a polymethacrylic board having a specific gravity which is about half of that of glass and is light, that it is easy to machine, and the like. Here, materials of the first substrate 1, the second substrate 2, and the third substrate 3 are not limited to polymethacryl styrene. In addition, the first substrate 1, the second substrate 2, and the third substrate 3 can be preferably formed of polystyrene, polymethyl methacrylate resins, polycarbonate, polycycloolefin, or the like that are excellent in transparency. For example, in the case of the first substrate 1 and the third substrate 3, lengths thereof in the X direction are 100 mm, lengths thereof in the Y direction are 80 mm, and lengths (thicknesses) thereof in the Z direction are 2 mm. For example, in the case of the second substrate 2, a length thereof in the X direction is 100 mm, a length thereof in the Y direction is 80 mm, and a length (a thickness) thereof in the Z direction is 5 mm.

As shown in FIG. 2, the separation tank 8 is a flow passage through which the buffer solution and the sample flow and extends in the X direction. As shown in FIG. 3, the separation tank 8 is formed by a concave portion that is provided at a central portion of a bottom 2*a* of the second substrate 2 in the Y direction. A width of the separation tank 8 in the Y direction is, for example, 10 mm. A depth of the separation tank 8 is, for example, 0.1 mm.

Figure 4:
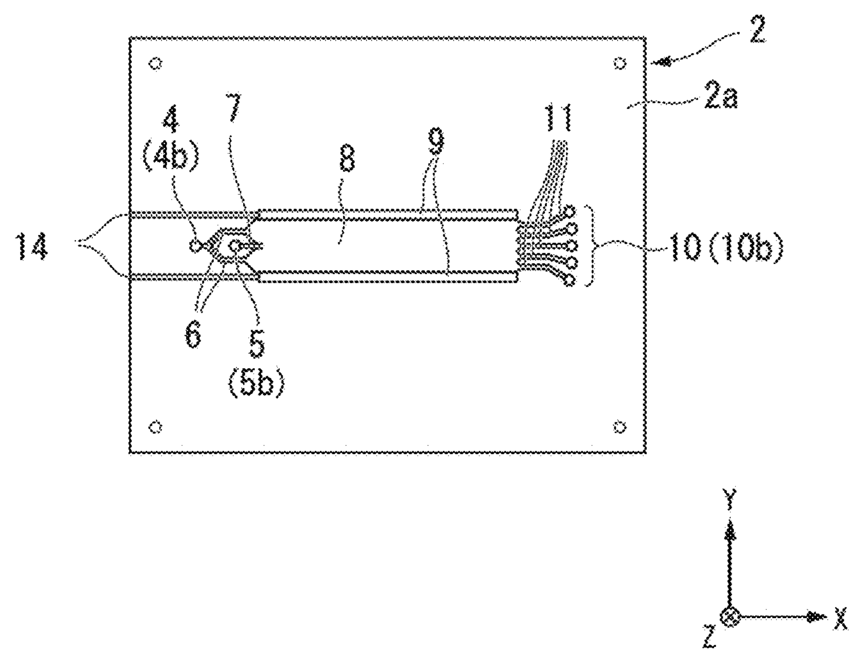
FIG. 4 is a bottom view of a second substrate 2 when the second substrate 2 is viewed from a bottom 2*a* side.
Figure 5:
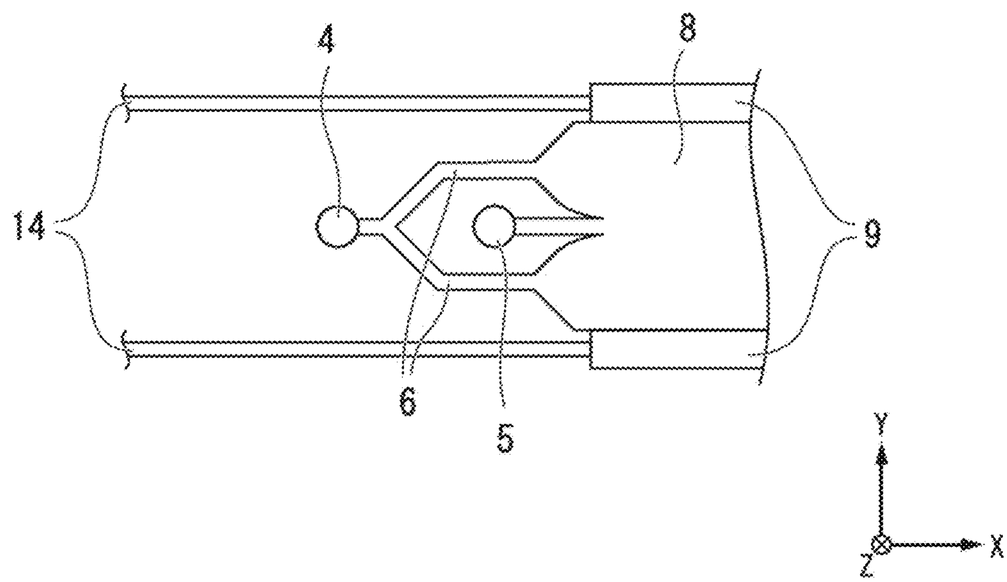
FIG. 5 is a partial enlarged view of a −X-side end portion of a separation tank 8 in FIG. 4.
Figure 6:
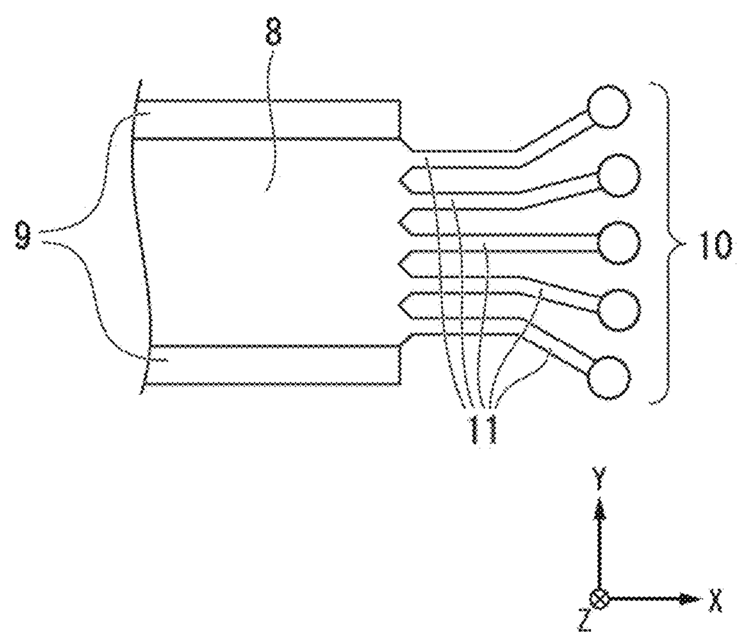
FIG. 6 is a partial enlarged view of a +X-side end portion of the separation tank 8 in FIG. 4.

FIG. 4 is a bottom view of the second substrate 2 when the second substrate 2 is viewed from the bottom 2*a* side. FIG. 5 is a partial enlarged view of a −X-side end portion of the separation tank 8 in FIG. 4. FIG. 6 is a partial enlarged view of a +X-side end portion of the separation tank 8 in FIG. 4.

A length of the separation tank 8 in the X direction is, for example, 50 mm.

Figure 7:
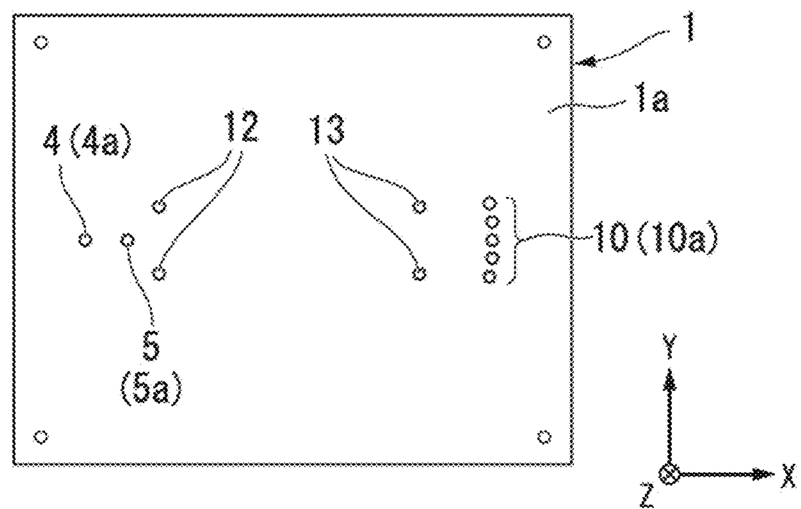
FIG. 7 is a bottom view of a first substrate 1 when the first substrate 1 is viewed from a bottom 1*a* side.

As shown in FIG. 4, the buffer solution introduction passages 6 and the sample introduction passage 7 are connected to the −X-side end portion of the separation tank 8. The sample introduction passage 7 extends in the X direction and one end thereof is connected to a central portion of the separation tank 8 in the Y direction. A depth of the sample introduction passage 7 is the same as the depth of the separation tank 8. The other end of the sample introduction passage 7 is connected to the sample introduction port 5. FIG. 7 is a bottom view of the first substrate 1 when the first substrate 1 is viewed from a bottom 1*a* side. The sample introduction port 5 extends in the vertical direction and is formed to pass through the first substrate 1 and the second substrate 2. The sample introduction port 5 includes through holes 5*a* formed in the first substrate 1 and through holes 5*b* formed in the second substrate 2 at the same position as the through holes 5*a* on an XY plane. The sample introduction port 5 is a site configured to introduce the above-described sample into the sample introduction passage 7.

One ends of the buffer solution introduction passages 6 are connected to the separation tank 8 at both sides of the sample introduction passage 7 in the Y direction. The other ends of the buffer solution introduction passages 6 are joined and are connected to the buffer solution introduction port 4. The buffer solution introduction port 4 extends in the vertical direction and is formed to pass through the first substrate 1 and the second substrate 2. The buffer solution introduction port 4 includes through holes 4*a* formed in the first substrate 1 and through holes 4*b* formed in the second substrate 2 at the same position as the through holes 4*a* on the XY plane. The buffer solution introduction port 4 is a site configured to introduce the buffer solution (a buffer) flowing through the separation tank 8 together with the above-described sample into the buffer solution introduction passages 6.

The plurality of (five in FIG. 4) sample collection passages 11 of which one ends are connected to the +X-side end portion of the separation tank 8 are provided. The sample collection passages 11 are provided at intervals in the Y direction. Positions of the separation tank 8 in the Y direction at which the sample collection passages 11 are connected to the separation tank 8 are set on the basis of mobility of the sample (exosomes) as will be described below. The other ends of the sample collection passages 11 are connected to the sample collecting parts 10.

The plurality of (five in FIG. 4) sample collecting parts 10 are provided at the sample collection passages 11. The sample collecting parts 10 extend in the vertical direction and are formed to pass through the first substrate 1 and the second substrate 2. The sample collecting parts 10 include through holes 10*a* formed in the first substrate 1 and through holes 10*b* formed in the second substrate 2 at the same position as the through holes 10*a* on the XY plane. The sample collecting parts 10 are sites configured to collect the sample (the exosomes) separated in accordance with electrophoretic mobility.

As shown in FIGS. 3 and 4, the electrode tanks 9 are disposed to communicate with both sides of the separation tank 8 in the Y direction. The electrode tanks 9 pass through the second substrate 2 in the vertical direction. For example, lengths of the electrode tanks 9 in the X direction are 50 mm, lengths thereof in the Y direction are 2 mm, and lengths (depths) thereof in the Z direction are 5 mm. Partition walls 17 are provided at bottoms of the electrode tanks 9, that is, at communicating portions with the separation tank 8. Upper sides of the electrode tanks 9 in relation to the partition walls 17 are second flow passages 30 through which a second buffer solution flows.

Movement of substances between the separation tank 8 and the electrode tanks 9 is blocked by the partition walls 17. Bottoms of the partition walls 17 are inclined surfaces 17*a* directed from the lower side toward the outside in the Y direction. The inclined surfaces 17*a* connect a position at which inner lateral surfaces 9*a* facing the electrode tanks 9 in the Y direction cross a bottom surface 8*a* of the separation tank 8 and a position at which outer lateral surfaces 9*b* facing the electrode tanks 9 in the Y direction cross the bottom 2*a* of the second substrate 2.

The partition walls 17 are formed of a gel material having ion permeability. A hydrogel having a high mechanical strength and uniformity is used, for example, as the gel material. A Tetra-PEG gel, a slide-ring (SR) gel, a nano-composite (NC) gel, a double network (DN) gel, or the like can be used, for example, as the hydrogel.

Also, terminals of gel polymers preferably have functional groups which can be chemically bonded to the base material. Examples of the functional groups of the terminals include an amino group, an isothiocyanate group, an isocyanate group, an acyl azide group, an N-hydroxysuccinimide ester group, a sulfonyl chloride group, an aldehyde group, an epoxide group, an oxirane group, a carbonate group, an aryl group, an imidoester group, a carbodiimide group, an anhydride group, a thiol group, a haloacetyl group, an alkyl halide group, a maleimide group, an aziridine group, an acryloyl group, a disulfide group, a diazoalkane group, a diazoacetyl group, a carbonyl diimidazole group, an N, N'-disuccinimidyl carbonate group, an N-hydroxy succinimidyl chloroformate group, hydrazine group, a hydrazide group, and the like.

Among them, the number of functional groups is preferably four or more, and types of polymers including four or more branched chains of a polyethylene glycol skeleton having functional groups at terminals thereof are more preferable. Examples of associated types of polymers include Tetra-PEG gels.

Figure 8:
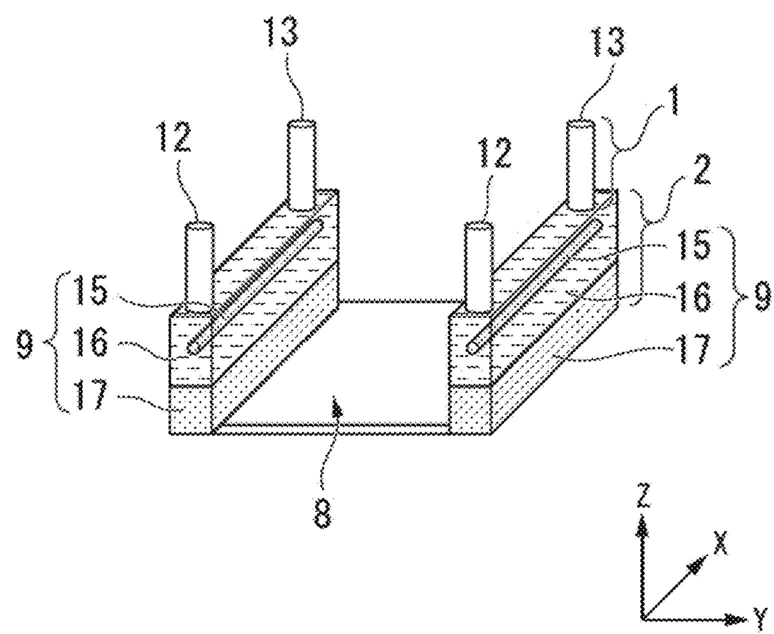
FIG. 8 is a view schematically showing a periphery of the separation tank 8 and electrode tanks 9.
Figure 9:
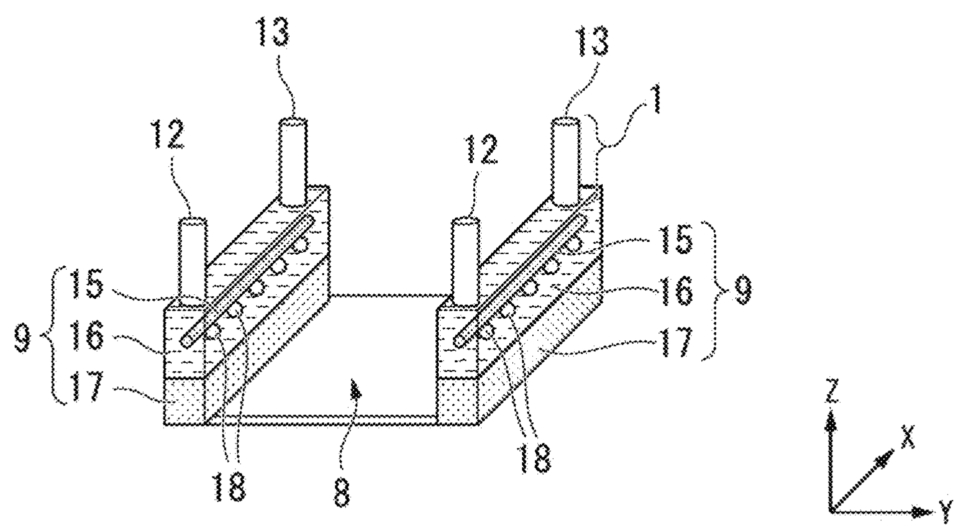
FIG. 9 is a view schematically showing a periphery of the separation tank 8 and the electrode tanks 9.
Figure 10:
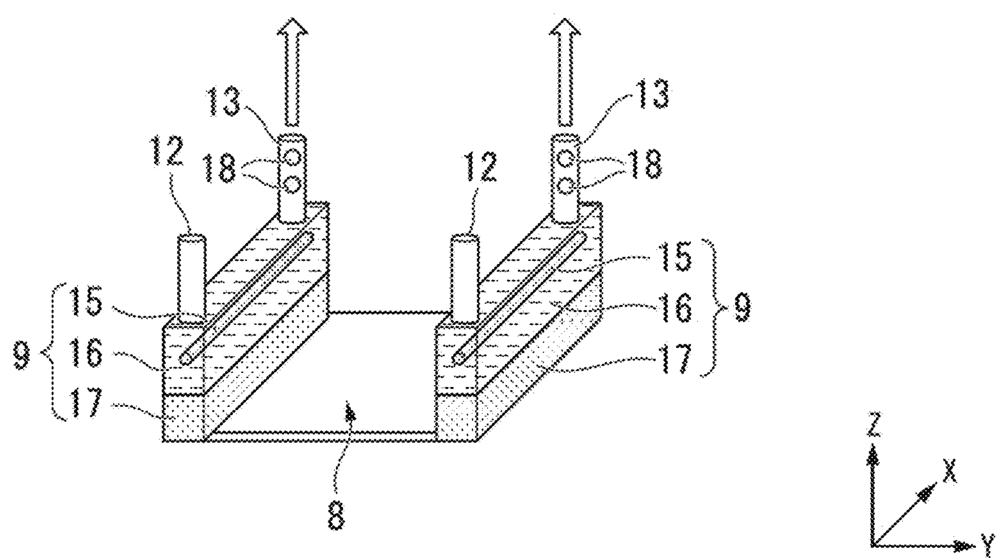
FIG. 10 is a view schematically showing a periphery of the separation tank 8 and the electrode tanks 9.

FIGS. 8 to 10 are views schematically showing a periphery of the separation tank 8 and the electrode tanks 9. The electrodes 15 are accommodated in the second flow passages 30 and a second buffer solution 16 flows through the second flow passages 30. The electrodes 15 are formed of, for example, a platinum wire. As shown in FIG. 2, electrode insertion ports 14 extending in the X direction at positions closer to an −X-side than the electrode tanks 9 are provided at the second substrate 2. Distal end sides of the electrodes 15 inserted through the electrode insertion ports 14 are accommodated in the second flow passages 30.

As shown in FIGS. 2 and 7 to 10, the second buffer solution introduction ports 12 communicating with the second flow passages 30 are provided to pass through the first substrate 1 in the vertical direction at a position of an −X-side end portion of the second flow passages 30 in the first substrate 1. The second buffer solution collection ports 13 communicating with the second flow passages 30 are provided to pass through the first substrate 1 in the vertical direction at a position of an +X-side end portion of the second flow passages 30 in the first substrate 1.

Referring again to FIG. 1, the sample supply system 61 supplies the sample to the sample introduction port 5 of the electrophoresis device DV via a tube 61*a*. In this embodiment, the sample supply system 61 supplies the sample containing the exosomes.

The buffer solution supply system 62 supplies the buffer solution to the buffer solution introduction passages 6 of the electrophoresis device DV via a tube 62*a*.

The sample collecting system 70 individually collects the sample and the buffer solution collected in the sample collecting parts 10 of the electrophoresis device DV in the plurality of sample collecting parts 10.

The second buffer solution supply system 80 supplies the second buffer solution to the second buffer solution introduction ports 12 of the electrophoresis device DV. The second buffer solution supply system 80 supplies the second buffer solution stored in a storage part 81 to the two second buffer solution introduction ports 12 via tubes 80*a* and 80*b* by driving a pump 82.

The second flow passage collecting system 90 collects substances (the second buffer solution, bubbles, and the like) in the second flow passages 30 of the electrophoresis device DV. The second flow passage collecting system 90 suctions the substances in the second flow passages 30 from two second buffer solution collection ports 13 of the electrophoresis device DV via a tube 90*a* by driving a pump 91 and collects the substances in a waste liquid part 92.

The voltage adjusting part 40 applies a voltage to the electrodes 15. The applied voltage is controlled by, for example, the controller CONT. The voltage adjusting part 40 applies a positive voltage to one electrode 15 of two electrodes 15 and applies a negative voltage to the other electrode 15 under the control of the controller CONT.

The microscope 50 irradiates the sample flowing through the separation tank 8 with a laser beam and acquires a particle image using Rayleigh scattered light. The microscope 50 outputs acquired image information to the controller CONT. The controller CONT calculates an electrophoresis speed, zeta potentials, and the like from the received image information. A detecting device configured to detect electrophoresis mobility is constituted of the microscope 50 and the controller CONT.

[Method for Manufacturing Electrophoresis Device DV]

Figure 11:
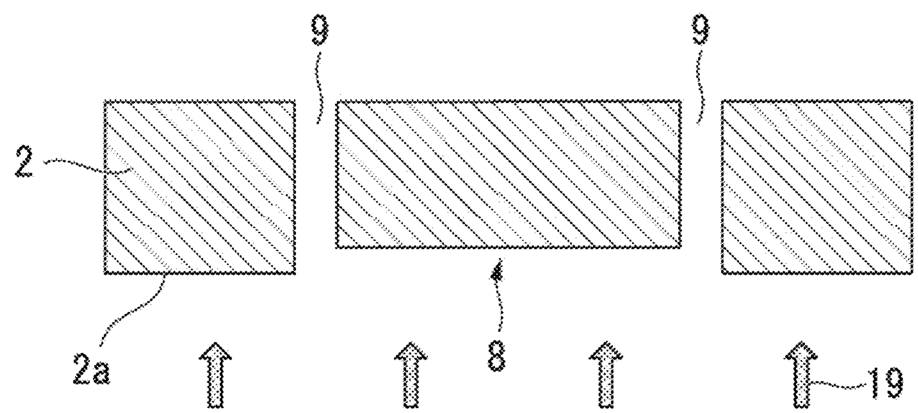
FIG. 11 is a view for describing a method for manufacturing the electrophoresis device DV.

Next, a method for manufacturing the above-described electrophoresis device DV will be described with reference to FIGS. 11 and 12.

The method for manufacturing the electrophoresis device DV includes a step of preparing the second substrate 2, a step of providing a mask material at the bottom 2*a* of the second substrate 2, a step of introducing a solution of a gel material, which does not gel, into the second flow passages 30 (the electrode tanks 9) of the second substrate 2 at which the mask material is provided, a step of removing the mask material after the gel material gels, and a step of stacking the first substrate 1 and the third substrate 3 on the second substrate 2.

Next, the steps will be described in detail.

The step of preparing the second substrate 2 includes a step of forming the separation tank 8, the electrode tanks 9, the buffer solution introduction passages 6, the sample introduction passage 7, the sample collection passages 11, the electrode insertion ports 14, and the through holes 4*b*, 5*b*, and 10*b* in the second base material 2. Cutting or injection molding can be adopted as a method for forming the separation tank 8, the electrode tanks 9, the buffer solution introduction passages 6, the sample introduction passage 7, the sample collection passages 11, the electrode insertion ports 14, and the through holes 4*b*, 5*b*, and 10*b* in the second base material 2.

Subsequently, the cut or injection molded second substrate 2 is immersed in ethanol and is cleaned for a predetermined period of time (for example, for one minute) using an ultrasonic cleaning machine. Subsequently, the second substrate 2 is rinsed using ultra-pure water and is blown using nitrogen. Subsequently, the second substrate 2 is exposed to toluene (for example, for about 12 to 13 minutes).

Note that (Acrycese (registered trademark) MS, JSP in Japan) is used as the polymethacryl styrene constituting the first substrate 1 to the third substrate 3.

Subsequently, the second substrate 2 is subject to oxygen plasma treatment. With regard to processing conditions thereof, for example, as shown in FIG. 11, the second substrate 2 is irradiated with oxygen plasma 19 from the bottom 2*a* side at an amount of oxygen of 30 cc and an output of 100 W for one minute using a plasma cleaner (PDC 210, Yamato Scientific Co., Ltd.) so that a surface of the second substrate 2 that is made of polymethacryl styrene having high hydrophobicity has a lyophilic property.

Figure 12:
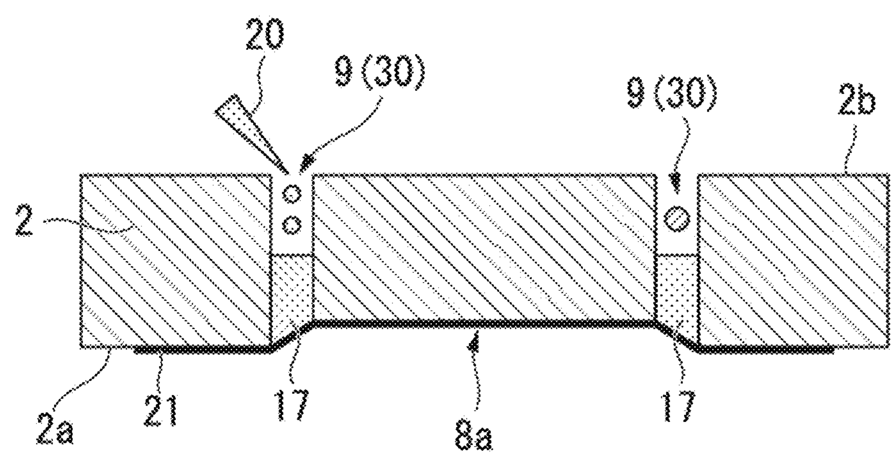
FIG. 12 is a view for describing the method for manufacturing the electrophoresis device DV.

As shown in FIG. 12, a mask material 21 is bonded on the second substrate 2 which has the surface having the lyophilic property across the bottom surface 8*a* of the separation tank 8 and the bottom 2*a* to close a bottom of the electrode tanks 9. Subsequently, a solution of the gel material is introduced through openings of the electrode tanks 9 (the second flow passages 30) open in the upper surface 2*b* using a pipette 20. In this embodiment, a Tetra-PEG gel is used as the gel material. The Tetra-PEG gel is a two liquid mixture type of hydrogel of a four arm type of polyethylene glycol (TA-PEG) solution having an amino group in terminals thereof and a four arm type of polyethylene glycol (TN-PEG) solution having an N-hydroxysuccinimidyl group in terminals thereof. The Tetra-PEG gel has a homogeneous network structure formed through an amide bond formed between the amino group of TA-PEG and an N-hydroxysuccinimidyl group of TN-PEG and has an excellent mechanical strength. In addition, the Tetra-PEG gel is firmly chemically bonded to a hydroxyl group or a carbonyl group of the above-described surface of the second substrate 2 through such functional groups, and thus the gel can be immobilized.

Also, since the Tetra-PEG gel has biocompatibility, suppression of adsorption of a biological substance in the gel is expected at a time of separating the biological substance as a sample.

Since the gel can be easily prepared using two-liquid mixing, there is an effect in that a process of manufacturing a device is not complicated.

In the case of TA-PEG SUNBRIGHT (registered trademark) PTE-100PA (NOF Corporation) is dissolved in a 0.2M sodium phosphate buffer at pH=7.4 so that a final concentration thereof is 100 mg/mL.

Also, in the case of TN-PEG, SUNBRIGHT (registered trademark) ITE-100HS (NOF Corporation) is dissolved in a 0.2M sodium citrate phosphate buffer at pH=5.8 so that a final concentration thereof is 100 mg/mL.

When the adjusted TA-PEG and TN-PEG solutions are mixed at 1:1, viscosity of the mixed solution increases within 10 minutes and a gelling reaction is checked.

After the above-described two liquid mixed solution (the gel solution) is introduced through the openings of the electrode tanks 9, air (bubbles) is removed from the gel solution so that the air does not remain and the above-described two liquid mixed solution is left to stand for about one hour until the above-described two liquid mixed solution gels with a stable strength. Subsequently, the mask material 21 is peeled off so that the gel material is not stuck thereto.

Subsequently, the second substrate 2 is adhered to the third substrate 3. Before the adhering, the third substrate 3 is immersed in ethanol as a pre-process and is cleaned using an ultrasonic cleaning machine for a predetermined period of time (for example, for one minute). Subsequently, the second substrate 2 is rinsed using ultra-pure water and is blown using nitrogen. Subsequently, the third substrate 3 is exposed to toluene (for example, for about 12 to 13 minutes). In addition, as in the second substrate 2, the third substrate 3 is subject to oxygen plasma treatment. Subsequently, the second substrate 2 and the third substrate 3 overlap and are pressurized and adhered at normal temperature at a pressure of 20 kN for 30 minutes using a nano-imprint device (NanoimPro; Graphene Platform, Japan).

The first substrate 1 is adhered to the second substrate 2 and the third substrate 3 which are adhered in this way. As shown in FIG. 7, as in the second substrate 2 and the third substrate 3, the first substrate 1 in which the second buffer solution introduction ports 12, the second buffer solution collection ports 13, and the through holes 4*a*, 5*a*, and 10*a* are formed in advance using cutting or injection molding is cleaned using ethanol. After that, the first substrate 1 is exposed to toluene or dichloroethane and then is subject to oxygen plasma treatment. Subsequently, the first substrate 1 is adhered to the second substrate 2 by applying a pressure of 20 kN to the substrates at normal temperature for 30 minutes using a nano-imprint device.

Subsequently, the electrophoresis device DV is manufactured by inserting the electrodes 15 through the electrode insertion ports 14 and accommodating the electrodes 15 in the second flow passages 30. The sample introduction port 5 and the sample supply system 61 in the electrophoresis device DV are connected to each other via the tube 61*a*. Similarly, the buffer solution introduction port 4 and the buffer solution supply system 62 are connected to each other via the tube 62*a*. Similarly, the second buffer solution introduction ports 12 and the pump 82 are connected to each other via the tubes 80*a* and 80*b*. In addition, the second buffer solution collection ports 13 and the pump 91 are connected to each other via the tube 90*a*, and the electrodes 15 are connected to the voltage adjusting part 40. Thus, separation of the sample using the device 100 for separating the extracellular vesicles is prepared.

In the case of the electrophoresis device DV, the hydrogel forming the gel material is firmly fixed to the second substrate 2 through chemical bonding therewith. Furthermore, in the case of the electrophoresis device DV, damage is not generated at an interface between the gel material and the second substrate 2 due to a high mechanical strength of the Tetra-PEG gel derived from the homogeneous network structure even if the gel material is dried in a dry environment. Even if the gel material is dried, the buffer solution is immersed immediately before the electrophoresis device DV is used so that the hydrogel can return to a wet state without a mechanical defect.

[Method for Separating Extracellular Vesicles]

Next, a method for separating extracellular vesicles using the above-described device 100 for separating the extracellular vesicles will be described.

Here, an experiment in which rhodamine B serving as a fluorescent dye, which does not have a charge, and sulforhodamine B, which has a negative charge, were separated as samples was performed.

A mixed solution of 1 mM rhodamine B and 1 mM sulforhodamine B was introduced from the sample supply system 61 to the sample introduction port 5. At this time, a 10 mM phosphate buffer solution was introduced from the buffer solution supply system 62 to the buffer solution introduction port 4 and a flow of the mixed solution of the rhodamine B and the sulforhodamine B was regulated.

Flow rates of the samples were set to 2 μL/min, and a flow rate of the buffer solution was set to 50 μL/min.

A voltage of 0 to 80 V was applied to the electrodes 15.

A phosphate buffer solution was introduced from the second buffer solution introduction ports 12 to the second flow passages 30, and the phosphate buffer solution was collected from the second buffer solution collection ports 13. When the voltage was applied to the electrodes 15, bubbles 18 were generated through electrolysis as shown in FIG. 9. However, an inside of the second flow passages 30 was suctioned by driving the pump 91 so that the phosphate buffer solution could be collected and the bubbles 18 could be removed as shown in FIG. 10. In addition, it was possible to prevent the bubbles 18 from being introduced into the separation tank 8 and thus adversely affecting separation of the samples.

Particularly, in this embodiment, a gel material constituting the partition walls 17 was chemically and firmly bonded to the second substrate 2. Thus, even if a hydraulic pressure in the second flow passages 30 was increased due to introduction/flow of the phosphate buffer solution, movement of substances (the buffer solution and the bubbles 18) between the separation tank 8 and the second flow passages 30 could be blocked.

The microscope 50 performed fluorescence observation on a position which was 40 mm away from the sample introduction port 5 toward an +X side thereof, and the position was captured using a digital camera for a microscope.

An excitation wavelength of the microscope 50 was 540 to 580 nm and a fluorescence wavelength thereof was 600 to 660 nm.

Figure 13:
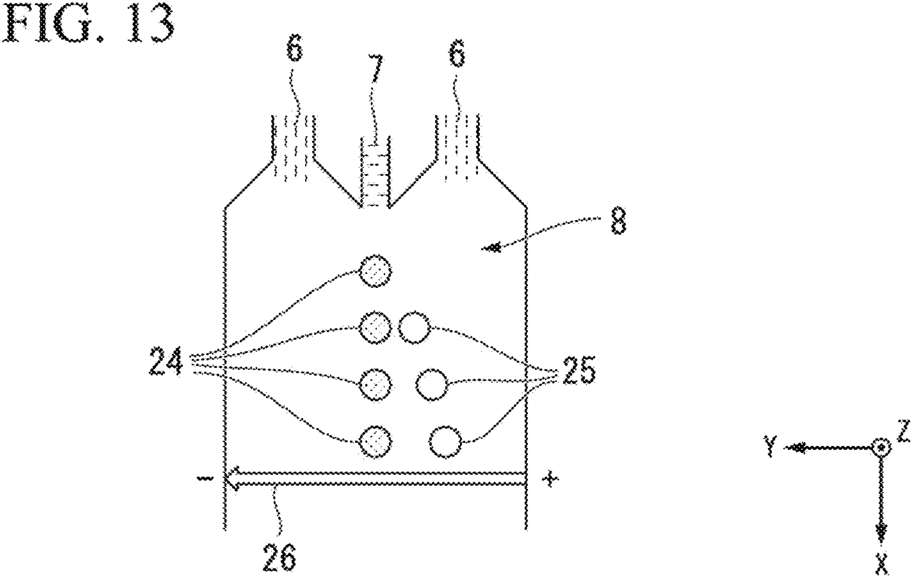
FIG. 13 is a view showing movement loci of rhodamine B24 and sulforhodamine B25 when an electric field 26 is formed.

FIG. 13 is a view schematically showing movement loci of rhodamine B24 and sulforhodamine B25 when an electric field 26 is formed in a direction in which it crosses the separation tank 8 due to an application of voltage to the electrodes 15. As shown in FIG. 13, it was checked that uncharged rhodamine B24 flowed to the +X side (a downstream side) serving as an introduction direction from the sample introduction passage 7 without being affected by the electric field, but sulforhodamine B25 having a negative charge flowed to a downstream side while moving to a positive electrode side.

Figure 14:
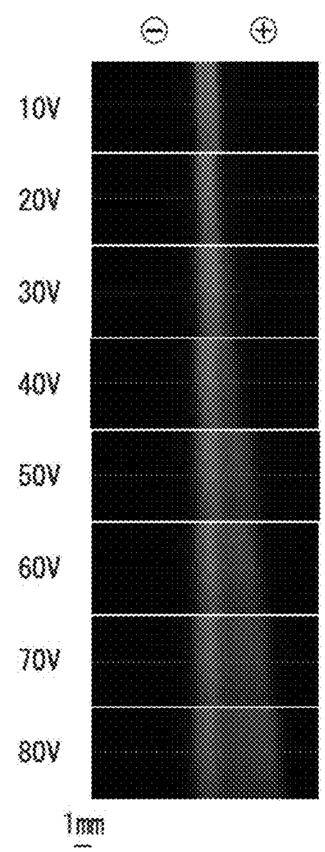
FIG. 14 is a fluorescence image when an applied voltage is changed and a movement locus of a sample is stabilized.
Figure 15:
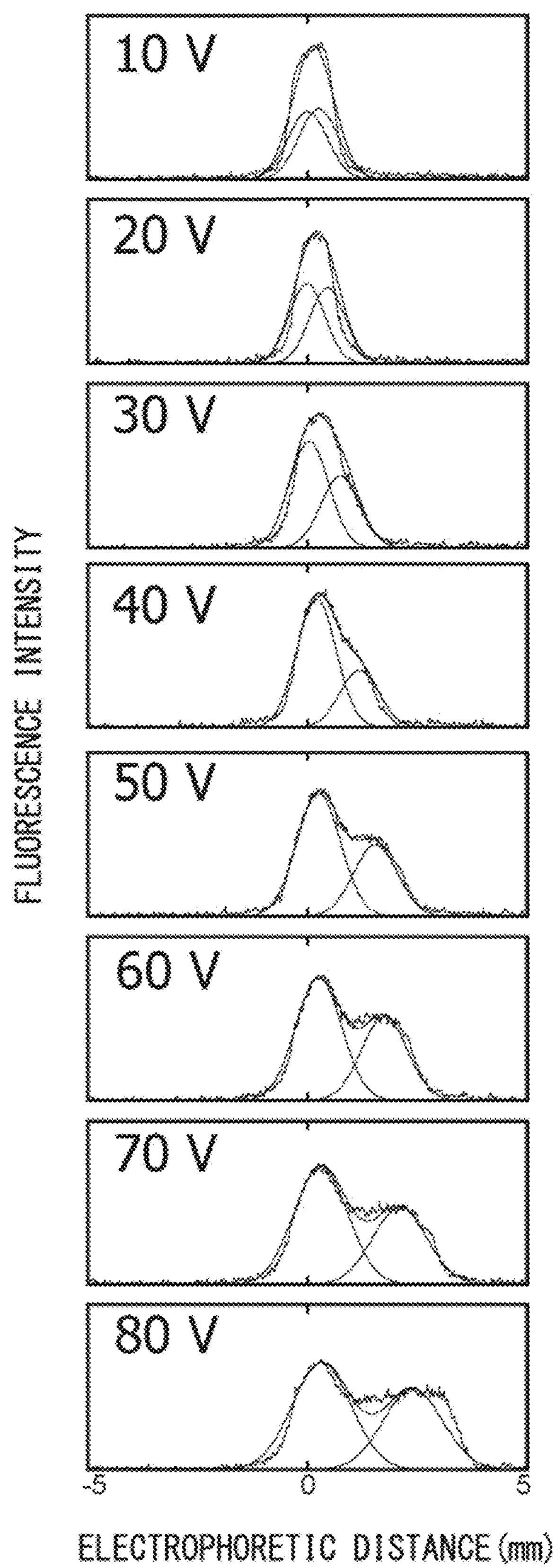
FIG. 15 is a view illustrating fluorescence intensity distributions of a sample when an applied voltage is changed.

FIG. 14 is a fluorescence image when an applied voltage to the electrodes 15 is changed from 0 to 80 V at an interval of 10 V and movement loci of samples are stabilized, and FIG. 15 is a view illustrating electrophoretic distances (fluorescence intensity distributions) of the samples. As shown in FIGS. 14 and 15, it was observed that peak positions of fluorescence intensities of the rhodamine B were not changed, whereas peak positions of fluorescence intensities of the sulforhodamine B moved toward the positive electrode along with an increase of the applied voltage.

A fluorescence intensity profile was analyzed to investigate a relationship between the applied voltage and a peak-to-peak distance between both of the samples.

Peak separation was performed, an electrophoretic distance between both peak positions was calculated, and a degree of separation R was obtained from the following Expression under the assumption that a fluorescence intensity distribution follows a normal distribution.

$$R = \frac{d_1 - d_2}{\frac{1}{2}(W_1 + W_2)} \quad \text{[Math. 1]}$$

In the foregoing Expression, d (d1, d2) is a position in the Y direction serving as a peak and W (W1, W2) is a half value width.

Figure 16:
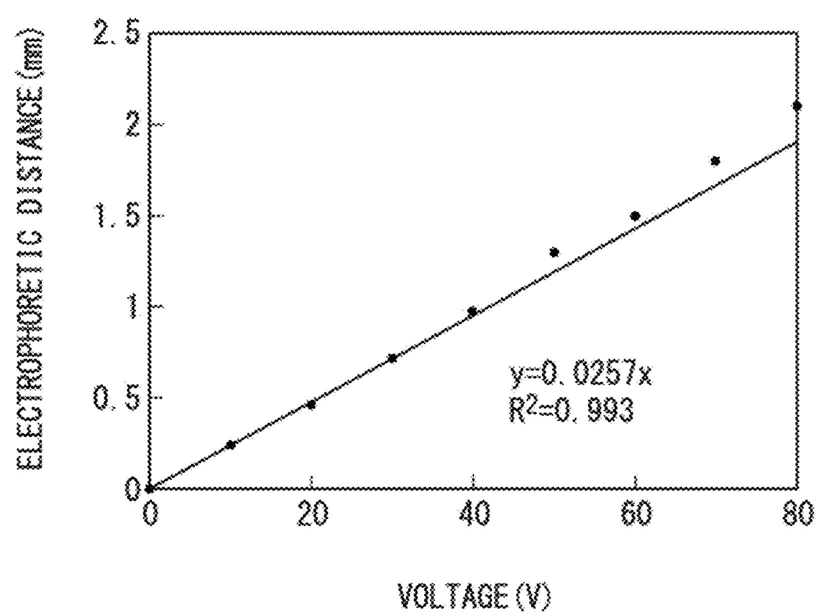
FIG. 16 is a view showing a relationship between applied voltages and electrophoretic distances of a sample.
Figure 17:
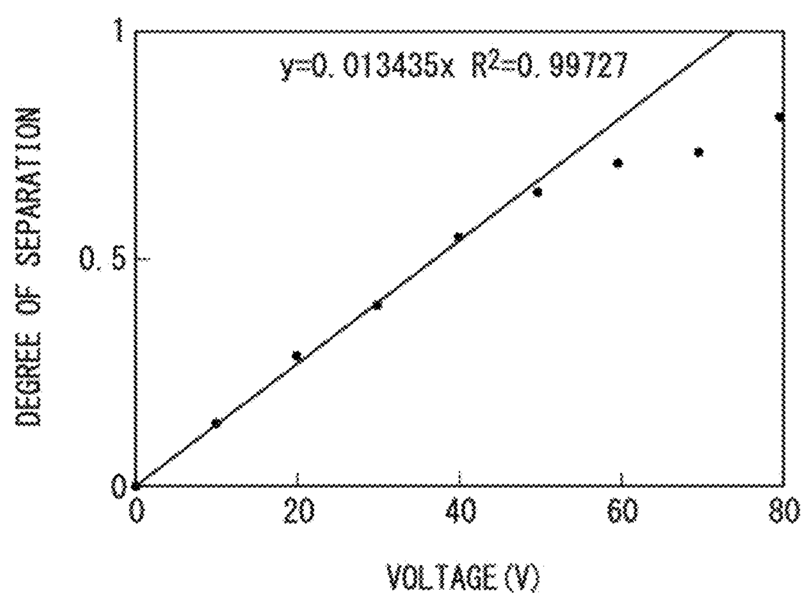
FIG. 17 is a view showing a relationship between applied voltages and degrees of separation of a sample.

FIG. 16 is a view showing a relationship between applied voltages and electrophoretic distances of samples. FIG. 17 is a view showing a relationship between the applied voltages and degrees of separation of the samples.

As shown in FIGS. 16 and 17, it was checked that both the electrophoretic distances and the degrees of separation had linear relationships at an applied voltage of 50 V or less.

On the other hand, it was checked that both the electrophoretic distances and the degrees of separation had nonlinear relationships at an applied voltage greater than 50 V. This is considered likely to be due to an influence of Joule's heat.

From this result, it was checked that an electric field, which does not cause disturbance, can be applied to the separation tank 8 and that the electrophoresis device DV performed a good separation operation within a voltage range up to 50 V.

Also, electrophoretic mobility of the sulforhodamine B was calculated as $1.6\times10^{-8}$ $m^2V^{-1}s^{-1}$ in consideration of an inclination of the graph, the applied voltages, a voltage efficiency of 55.4%, and an applying time of 29.5 s.

A zeta potential 4 was calculated from the following Smoluchowski's equation using such electrophoretic mobility.

$$\xi=\eta\times\mu/(\varepsilon0\times\varepsilon r)$$

Here, ξ is a zeta potential, q is a viscosity coefficient, ε0 is a dielectric constant in vacuum, and εr is a relative dielectric constant. The viscosity coefficient is η=0.89×10-3 kg/m2s, the relative dielectric constant is εr=78.5, the dielectric constant in vacuum is $\varepsilon0=8.854\times10^{12}$ $m^{-3}kg^{-1}s^4A^2$ assuming that values of a viscosity coefficient and a relative dielectric constant of a phosphate buffer solution are the same as those of water at 25° C. Thus, the zeta potential of the sulforhodamine B was calculated as =20.5 mV.

As described above, in this embodiment, the gel material having ion permeability is provided at communicating portions between the separation tank 8 and the electrode tanks 9 (the second flow passages 30) as the partition walls 17 with a predetermined bonding strength. Thus, a buffer solution and bubbles can be prevented from moving between the separation tank 8 and the electrode tanks 9. In addition, electrophoresis and a separation operation of samples can be stably performed for a long period of time. Particularly, in this embodiment, the gel material is formed as the hydrogel. Thus, the hydrogel is chemically bonded and firmly adhered to the second substrate 2. In addition, even if a hydraulic pressure along with a flow of the samples and the buffer solution in the separation tank 8 or a flow of the buffer solution in the second flow passages is increased, movement of the buffer solution and the bubbles between the separation tank 8 and the second flow passages 30 can be stably blocked for a long period of time. Furthermore, the hydrogel is impregnated in the buffer solution before the samples are separated even after the hydrogel has dried so that the hydrogel can return to a wet state without mechanical defects. Thus, the hydrogel is easily stored in a dry state, and for example, the hydrogel can also be stored in a simple method in the field of medicine.

Also, in the electrophoresis device DV related to this embodiment, positions of the sample collecting parts 10 and the sample collection passages 11 in the Y direction are appropriately set in accordance with electric mobilities of samples so that, for example, even if a sample in which a plurality of types of exosomes are mixed is used, the exosomes can be easily separated and collected in the sample collecting parts 10 and the sample collection passages 11 corresponding to the electric mobilities of the exosomes. Furthermore, when the electrophoresis device DV, in which the positions of the sample collecting parts 10 and the sample collection passages 11 in the Y direction are fixed, is used, a voltage of an intensity in which a plurality of the types of exosomes can be sufficiently separated can be applied or a flow rate of the sample in the separation tank 8 can be adjusted. In this embodiment, the first substrate 1 to the third substrate 3 are formed of polymethacryl styrene serving as a synthetic resin material. Thus, various shapes can be easily obtained using a method such as cutting or injection molding and manufacturing costs can also be reduced.

Modified Example of Method for Manufacturing Electrophoresis Device DV

Next, a modified example of the above-described method for manufacturing the electrophoresis device DV will be described with reference to FIGS. 18 to 21. Note that a description of the same procedure as in the above-described method for manufacturing the electrophoresis device DV will be simplified or omitted.

A method for manufacturing the electrophoresis device DV of this modified example includes a step of preparing the first substrate 1 and the second substrate 2, a step of providing the mask material 21 at the upper surface 2*b* of the second substrate 2, a step of introducing a solution of a gel material, which does not gel, into the second flow passages 30 (the electrode tanks 9) of the second substrate 2, at which the mask material is provided, a step of removing the mask material 21 after the gel material gels, and a step of stacking the first substrate 1 and the third substrate 3 on the second substrate 2.

Figure 18:
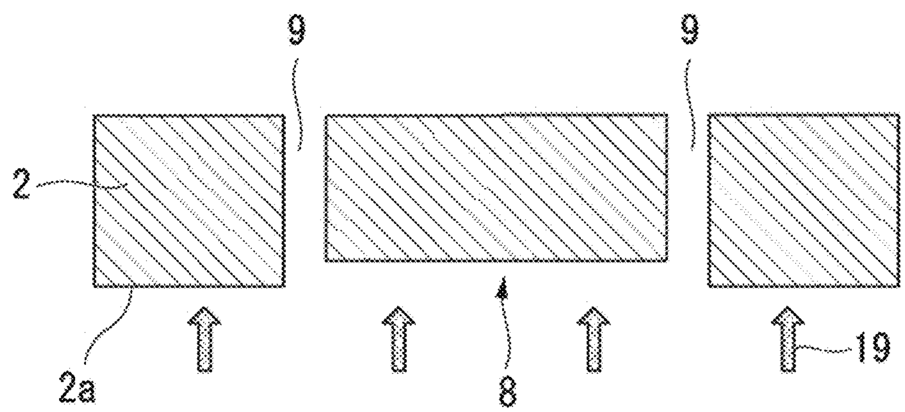
FIG. 18 is a view for describing a modified example of the method for manufacturing the electrophoresis device DV.

As described above, the second substrate 2, in which the separation tank 8, the electrode tanks 9, the buffer solution introduction passages 6, the sample introduction passage 7, the sample collection passages 11, the electrode insertion ports 14, and the through holes 4*b*, 5*b*, and 10*b* are formed, is prepared, is immersed in ethanol, and is cleaned using an ultrasonic cleaning machine for 10 minutes. Subsequently, the second substrate is rinsed twice using ultra-pure water, is blown using nitrogen, and is exposed to dichloroethane for three minutes. Subsequently, as shown in FIG. 18, the second substrate 2 is subject to oxygen plasma treatment.

Figure 19:
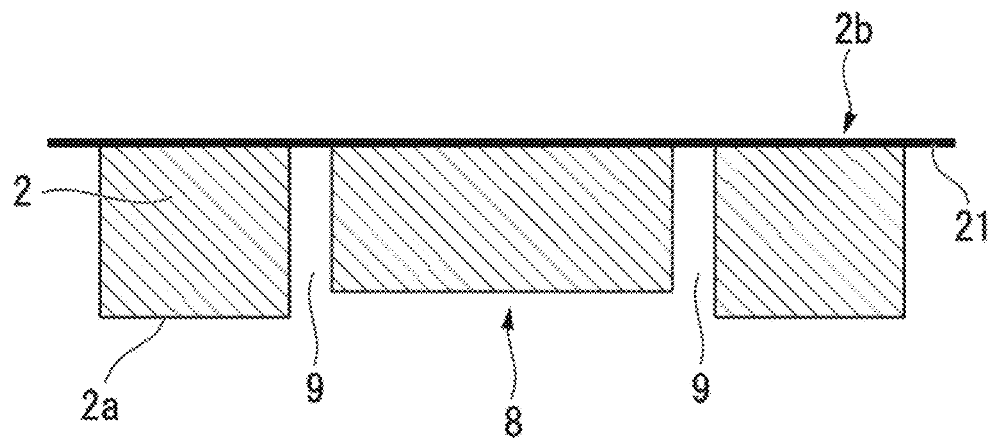
FIG. 19 is a view for describing a modified example of the method for manufacturing the electrophoresis device DV.
Figure 20:
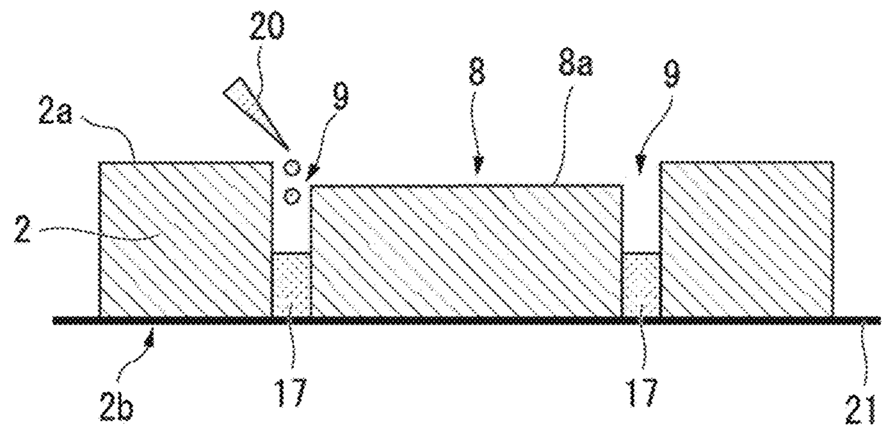
FIG. 20 is a view for describing a modified example of the method for manufacturing the electrophoresis device DV.

Subsequently, as shown in FIG. 19, the mask material 21 is bonded to the upper surface 2*b* of the second substrate 2. Subsequently, after the second substrate 2 is reversed such that the mask material 21 and the upper surface 2*b* is at a lower side thereof, as shown in FIG. 20, the above-described solution of the gel material is introduced through an opening of the electrode tanks 9 open at the bottom 2*a* using the pipette 20. For example, an amount of the gel solution introduced into the electrode tanks 9 is an amount in which the gelling partition walls 17 and the bottom surface 8*a* of the separation tank 8 become one surface. When the gel solution gels, the mask material 21 is peeled off such that the gel material is not adhered thereto. Thus, the partition walls 17 are formed of the gel material, one end thereof at a Z side is flush with the upper surface 2*b* of the second substrate 2, and the other end thereof is flush with the bottom surface 8*a*.

Figure 21:
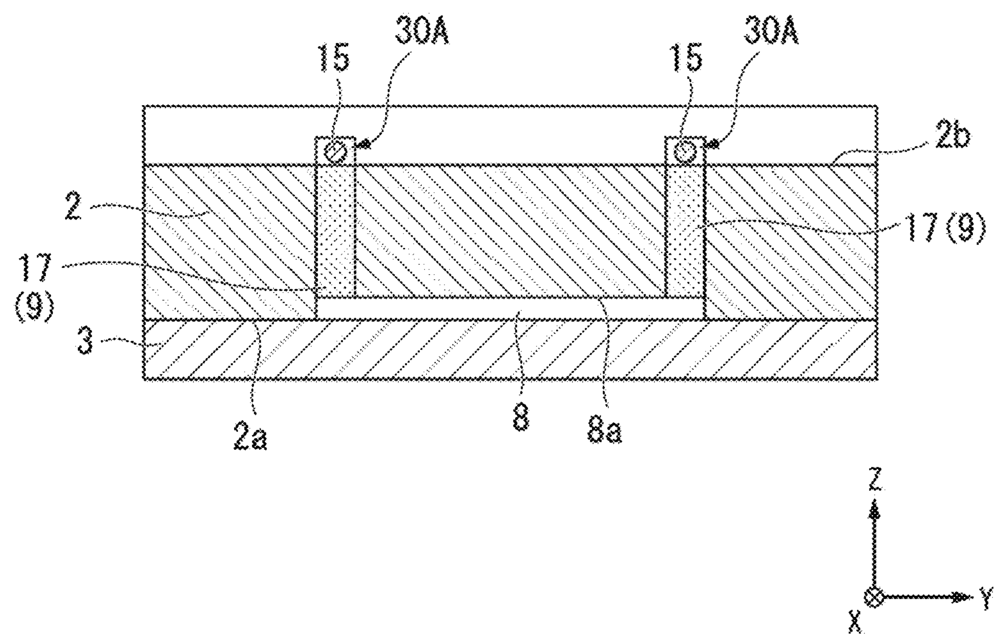
FIG. 21 is a view for describing a modified example of the method for manufacturing the electrophoresis device DV.

Subsequently, as in the above-described manufacturing method, the pre-processed third substrate 3 is adhered to the second substrate 2. Subsequently, the first substrate 1 is adhered to the adhered second substrate 2 and third substrate 3. FIG. 21 shows a view of the second substrate 2 when it is reversed again such that the upper surface 2*b* of the second substrate 2 is at an upper side thereof.

As shown in FIG. 21, grooves extending in the X direction are formed at positions of the first substrate 1 opposite to the partition walls 17 as second flow passages 30A. The electrodes 15 are inserted and accommodated in the second flow passages 30A through the electrode insertion ports 14.

In the manufacturing method of this modified example, the same action and effect as in the above-described manufacturing method are obtained. In addition, the second flow passages 30A are formed in the first substrate 1, and distances between the second flow passages 30A and the separation tank 8 are increased. Thus, movement of a buffer solution and bubbles between the separation tank 8 and second flow passages 30A is easily blocked.

Although preferable embodiments of the present invention have been described in detail above, the present invention is not limited to such specific embodiments. In addition, various modifications and changes are possible within the range of the gist of the present invention disclosed in the appended claims.

REFERENCE SIGNS LIST

1 First substrate (second base material)
2 Second substrate (base material)
3 Third substrate (third base material)
8 Separation tank (first flow passage)
9 Electrode tank
10 Sample collecting part
15 Electrode
17 Partition wall
30, 30A Second flow passage
40 Voltage adjusting part (adjusting part)
61 Sample supply system
62 Buffer solution supply system
70 Sample collecting system
80 Second buffer solution supply system
90 Second flow passage collecting system
100 Device for separating extracellular vesicles
DV Electrophoresis device

The invention claimed is:

1. An electrophoresis device comprising:

a first flow passage extending in a first direction and through which a sample and a buffer solution flow;

a sample collecting part provided at an end portion of the first flow passage and configured to collect the sample;

electrodes disposed at both sides of the first flow passage in a second direction perpendicular to the first direction and configured to apply a voltage to the first flow passage in the second direction;

second flow passages communicating with both sides of the first flow passage in the second direction, configured to accommodate the electrodes, and through which a second buffer solution flows; and partition walls fixed to communicating portions between the first and second flow passages with a predetermined bonding strength and configured to block movement of substances between the first and second flow passages, wherein the first flow passage and the second flow passages are formed of a base material, the partition walls are formed of a gel material having ion permeability, and being chemically bonded to the base material, openings of the second flow passages are provided at a first surface of the base material in a third direction which is perpendicular to the first and second directions, openings of the first flow passage is provided at a second surface of the base material in the third direction, the second flow passages are disposed to communicate with the first flow passage in the third direction, a second base material is stacked on the first surface of the base material, and a third base material is stacked on the second surface of the base material.

2. The electrophoresis device according to claim 1, wherein the gel material includes a hydrogel, and the base material includes a synthetic resin.

3. The electrophoresis device according to claim 1, wherein the gel material is fixed to communicating portions between the first flow passage and the second flow passages with a bonding strength to block movement of the buffer solution, the second buffer solution, and bubbles between the first flow passage and the second flow passages.

4. The electrophoresis device according to claim 1, wherein the position of the sample collecting part in the second direction is set based on electrophoretic distance of the sample when the voltage is applied to the sample.

5. A device for separating extracellular vesicles comprising:

the electrophoresis device according to claim 1;

a sample supply system configured to supply a sample including extracellular vesicles to the first flow passage;

a buffer solution supply system configured to supply the buffer solution to the first flow passage;

a sample collecting system configured to collect the sample via the sample collecting part;

a second buffer solution supply system configured to supply the second buffer solution to one ends of the second flow passages;

a second flow passage collecting system configured to collect substances in the second flow passages from the other ends of the second flow passages; and an adjusting part configured to adjust the voltage applied through the electrodes.

6. The device for separating extracellular vesicles according to claim 5, comprising:

a detecting device configured to detect mobility of the extracellular vesicles due to the application of the voltage.

7. A method for manufacturing an electrophoresis device comprising:

a step of preparing a base material including a first flow passage extending in a first direction and through which a sample and a buffer solution flow and second flow passages communicating with both sides of the first flow passage in a second direction perpendicular to the first direction and through which a second buffer solution flows; and openings of the second flow passages are provided at a first surface of the base material in a third direction which is perpendicular to the first and second directions, openings of the first flow passage is provided at a second surface of the base material in the third direction, the second flow passages are disposed to communicate with the first flow passage in the third direction, a step of fixing a gel material having ion permeability and a predetermined bonding strength to communicating portions between the first flow passage and the second flow passages as partition walls configured to block movement of substances between the first flow passage and the second flow passages, and a step of stacking a second base material on the first surface of the base material and stacking a third base material on the second surface of the base material after the step of fixing the gel material.

8. The method for manufacturing an electrophoresis device according to claim 7, wherein the step of fixing the gel material includes: a step of providing a mask material at a boundary between the gel material and the first flow passage when the second surface is at a lower side;

a step of introducing a solution of the gel material, which does not gel, to the base material of which the second surface is at the lower side through the openings of the second flow passages of the first surface; and a step of removing the mask material after the gel material gels.

9. The method for manufacturing an electrophoresis device according to claim 7, wherein the step of fixing the gel material includes: a step of providing a mask material at the first surface and closing the openings of the second flow passages;

a step of introducing a solution of the gel material, which does not gel, to the base material of which the first surface is at a lower side through the openings of the second flow passages of the second surface; and a step of removing the mask material after the gel material gels.

10. The method for manufacturing an electrophoresis device according to claim 7, comprising:

a step of providing a lyophilic property to a surface of the base material with respect to the solution of the gel material, which does not gel, before the step of fixing the gel material.

11. The method for manufacturing an electrophoresis device according to claim 7, comprising:

the second flow passages are configured to accommodate the electrodes configured to apply a voltage to the first flow passage in the second direction, the base material includes the sample collecting part provided at an end portion of the first flow passage and configured to collect the sample, the position of the sample collecting part in the second direction is set based on electrophoretic distance of the sample due to the application of the voltage.

* * * * *